United States Patent
Ching et al.

(10) Patent No.: US 6,481,262 B2
(45) Date of Patent: Nov. 19, 2002

(54) STENT CRIMPING TOOL

(75) Inventors: Denise Ching, San Jose, CA (US); Richard S. Stack, Chapel Hill, NC (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/886,840

(22) Filed: Jun. 20, 2001

(65) Prior Publication Data

US 2002/0124626 A1 Sep. 12, 2002

Related U.S. Application Data

(62) Division of application No. 09/475,694, filed on Dec. 30, 1999, now abandoned.

(51) Int. Cl.[7] .............................................. B21D 39/04
(52) U.S. Cl. ........................................... 72/416; 29/282
(58) Field of Search ............................. 72/416; 29/282, 29/283.5, 243.517; 606/1, 108, 198

(56) References Cited

U.S. PATENT DOCUMENTS

| | | | |
|---|---|---|---|
| 141,992 A | 8/1873 | Carr | |
| 579,214 A | 3/1897 | Adams | |
| 696,289 A | 3/1902 | Williams | |
| 852,290 A | 4/1907 | Neal | |
| 915,184 A | 3/1909 | Keirn | |
| 1,045,886 A | 12/1912 | Reay | |
| 1,051,777 A | * 1/1913 | Mars | 72/416 |
| 1,230,561 A | 6/1917 | Chige | |
| 1,268,171 A | 6/1918 | Spaulding | |
| 1,758,261 A | 5/1930 | Leland | |
| 1,966,593 A | 1/1934 | O'Russa | |
| 2,419,678 A | * 4/1947 | Duenas et al. | 72/416 |
| 2,452,857 A | 11/1948 | Mesaros | |

(List continued on next page.)

FOREIGN PATENT DOCUMENTS

| | | |
|---|---|---|
| CA | 2211694 | 2/1998 |
| DE | 297 14 857 U | 10/1997 |
| EP | 0 303 889 B1 | 2/1989 |
| EP | 0 303 889 A2 | 2/1989 |
| EP | 0 562 478 A1 | 9/1993 |
| EP | 0 630 623 A3 | 12/1994 |
| EP | 0 630 623 A2 | 12/1994 |
| EP | 0 826 346 A1 | 3/1998 |
| EP | 0 873 731 A1 | 10/1998 |
| EP | 0 938 880 A2 | 9/1999 |
| EP | WO 01/21076 A  * | 3/2001 |
| FR | 975 797 A | 3/1951 |
| GB | 159065 | 2/1921 |
| GB | 2 088 811 A | 6/1982 |
| SU | 127831 | 6/1989 |
| SU | 1488086 | 6/1989 |
| WO | WO 97/09946 | 3/1997 |
| WO | WO 98/14120 | 4/1998 |
| WO | WO 98/19633 | 5/1998 |

OTHER PUBLICATIONS

C. R. Bard Brochure, The Extraordinary Stent (Undated).

*Primary Examiner*—Daniel C. Crane
(74) *Attorney, Agent, or Firm*—Fulwider Patton Lee & Utecht, LLP

(57) ABSTRACT

A stent crimping device for crimping a stent onto a balloon delivery-catheter of the kind typically used in percutaneous transluminal coronary angioplasty procedures. The device comprises a pair of plates bearing mutually opposed parallel ribs. The ribbed plates move in a direction such that a stepped circular crimp may be rolled onto a stent thereby firmly fixing the stent to a catheter balloon.

15 Claims, 3 Drawing Sheets

U.S. PATENT DOCUMENTS

| | | | |
|---|---|---|---|
| 2,465,433 A | | 3/1949 | Doniger |
| 2,553,479 A | | 5/1951 | Schrmarge et al. |
| 3,496,684 A | | 2/1970 | Banning et al. |
| 3,898,897 A | | 8/1975 | Jauhianinen |
| 4,016,738 A | | 4/1977 | Puchko |
| 4,047,420 A | * | 9/1977 | Edwards .................... 72/416 |
| 4,107,964 A | | 8/1978 | Smith |
| 4,215,871 A | | 8/1980 | Hirsch et al. |
| 4,468,224 A | | 8/1984 | Enzmann et al. |
| 4,576,142 A | | 3/1986 | Schiff |
| 4,644,936 A | | 2/1987 | Schiff |
| 4,681,092 A | | 7/1987 | Cho et al. |
| 4,697,573 A | | 10/1987 | Schiff |
| 4,901,707 A | | 2/1990 | Schiff |
| 4,907,336 A | | 3/1990 | Gianturco |
| 4,987,722 A | | 1/1991 | Koebbeman |
| 5,132,066 A | | 7/1992 | Charlesworth et al. |
| 5,133,732 A | | 7/1992 | Wiktor |
| 5,183,085 A | | 2/1993 | Timmermans |
| 5,189,786 A | | 3/1993 | Ishikawa et al. |
| 5,195,539 A | | 3/1993 | Dryud et al. |
| 5,209,143 A | | 5/1993 | Sweet |
| 5,217,434 A | | 6/1993 | Arney |
| 5,353,623 A | * | 10/1994 | Bobenhausen .............. 72/416 |
| 5,377,400 A | * | 1/1995 | Homm ....................... 72/416 |
| 5,437,083 A | | 8/1995 | Williams et al. |
| 5,456,667 A | | 10/1995 | Ham et al. |
| 5,458,615 A | | 10/1995 | Klemm et al. |
| 5,476,505 A | | 12/1995 | Limon |
| 5,540,124 A | | 7/1996 | Srhoj |
| 5,546,646 A | | 8/1996 | Williams et al. |
| 5,626,604 A | | 5/1997 | Cottone, Jr. |
| 5,630,830 A | | 5/1997 | Verbeek |
| 5,653,691 A | | 8/1997 | Rupp et al. |
| 5,672,169 A | | 9/1997 | Verbeek |
| 5,695,515 A | | 12/1997 | Orejola |
| 5,715,723 A | | 2/1998 | Owens |
| 5,725,519 A | | 3/1998 | Penner et al. |
| 5,738,674 A | | 4/1998 | Williams et al. |
| 5,746,764 A | | 5/1998 | Green et al. |
| 5,768,935 A | * | 6/1998 | Owens ....................... 72/416 |
| 5,783,227 A | | 7/1998 | Dunham |
| 5,785,715 A | | 7/1998 | Schatz |
| 5,787,572 A | | 8/1998 | Toms |
| 5,795,289 A | | 8/1998 | Wyttenbach |
| 5,810,838 A | | 9/1998 | Solar |
| 5,810,873 A | | 9/1998 | Morales |
| 5,836,952 A | | 11/1998 | Davis et al. |
| 5,860,966 A | | 1/1999 | Tower |
| 5,893,852 A | | 4/1999 | Morales |
| 5,893,867 A | | 4/1999 | Bagaoisan et al. |
| 5,911,452 A | | 6/1999 | Yan |
| 5,920,975 A | | 7/1999 | Morales |
| 5,938,696 A | | 8/1999 | Goicoechea et al. |
| 5,951,540 A | * | 9/1999 | Verbeek ....................... 606/1 |
| 5,972,016 A | | 10/1999 | Morales |
| 5,974,652 A | | 11/1999 | Kimes et al. |
| 6,009,614 A | | 1/2000 | Morales |
| 6,024,737 A | | 2/2000 | Morales |
| 6,063,102 A | | 5/2000 | Morales |
| 6,074,381 A | | 6/2000 | Dinh |
| 6,082,990 A | | 7/2000 | Jackson et al. |
| 6,092,273 A | | 7/2000 | Villareal |
| 6,125,523 A | | 10/2000 | Brown |

* cited by examiner

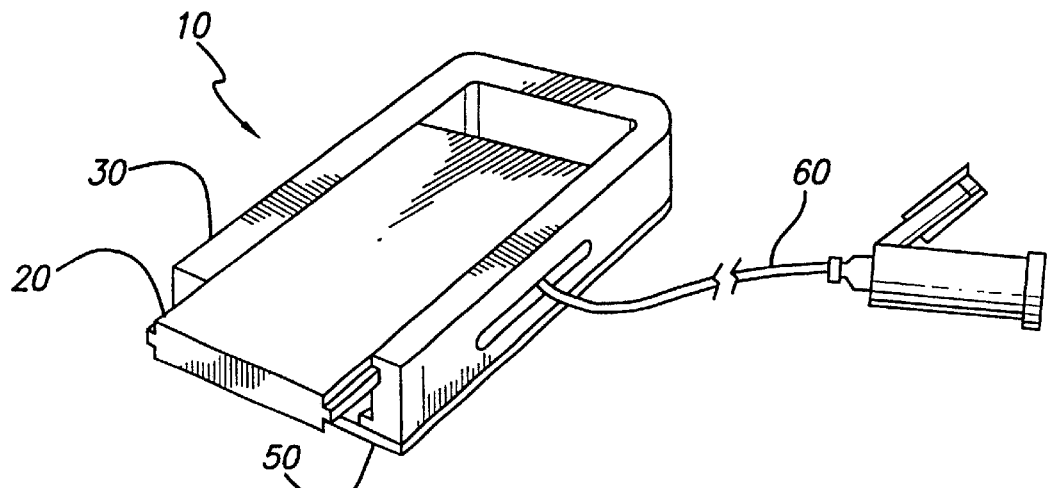
FIG. 1
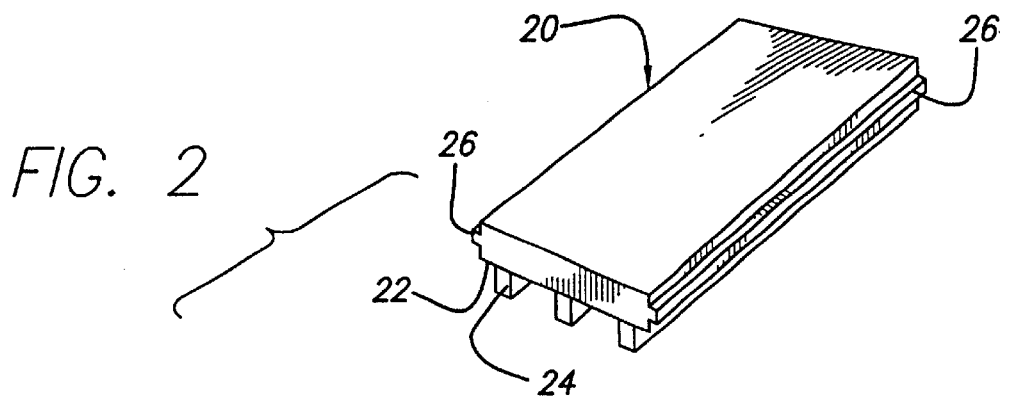
FIG. 2
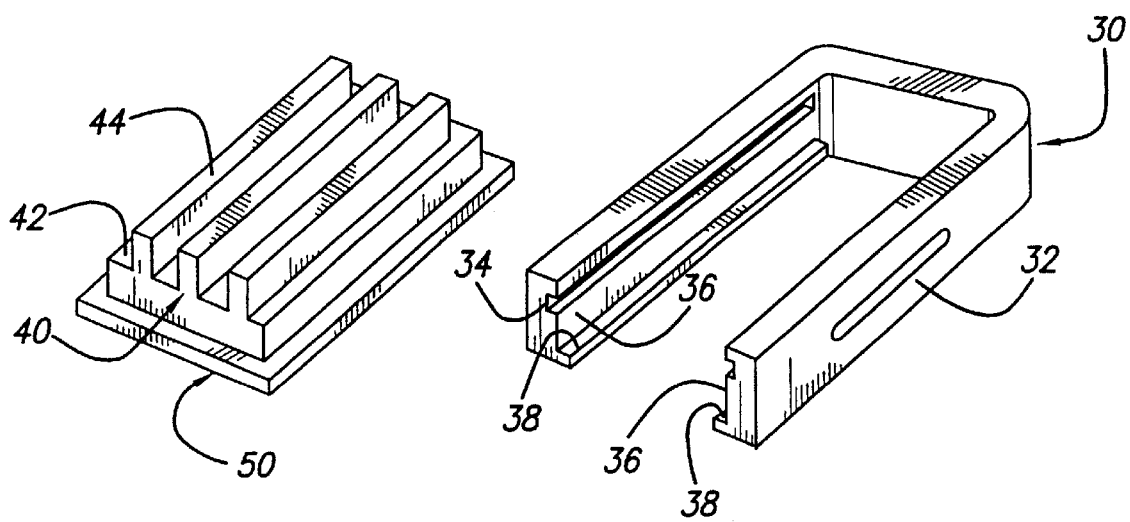

STENT CRIMPING TOOL

This application is a division of Ser. No. 09/475,694, filed Dec. 30, 1999, now abandoned.

BACKGROUND OF THE INVENTION

The present invention relates to the field of stent crimping devices generally and more particularly to a device for providing a stepped crimp at preselected locations along the axis of a stent.

A stent is an intravascular prosthesis that is delivered and implanted within a patient's vasculature by a balloon catheter. Stents are typically used in percutaneous transluminal coronary angioplasty ("PTCA") or percutaneous transluminal angioplasty ("PTA") procedures. Typical stents and delivery catheters are disclosed by U.S. Pat. No. 5,514,154 (Lau et al.), U.S. Pat. No. 5,569,295 (Lam) and U.S. No. 5,507,768 (Lau et al.) which are incorporated herein by reference.

In a typical PTCA procedure, for compressing lesion plaque against an artery wall to dilate the artery lumen, a guiding catheter is percutaneously introduced into the cardiovascular system of a patient through the brachial or femoral arteries and advanced through the vasculature until the distal end is in the ostium of the aorta. A guidewire and a dilation catheter having an expandable member, such as a balloon located on its distal end, are introduced through the guiding catheter with the dilation catheter slidingly disposed on the guidewire. The guidewire is first advanced out of the guiding catheter into the patient's coronary vasculature, and the dilation catheter is advanced over the previously advanced guidewire until the dilation balloon is positioned across the lesion. Once in position, the balloon is inflated to a predetermined size with radiopaque liquid at relatively high pressures to radially compress the atherosclerotic plaque of the lesion against the inside of the artery wall and thereby dilate the lumen of the artery. The balloon is then deflated to a low profile, so that the dilation catheter can be withdrawn and blood flow resumed within the dilated artery. While this procedure is typical, it is not the only method used in angioplasty.

In angioplasty procedures of the kind referenced above, restenosis of the artery may develop over several months, which may require another angioplasty procedure, a surgical bypass operation, or some procedure for repairing or strengthening the area. To reduce the chance of restenosis and strengthen the area, a stent may be introduced to maintain the patency of the lumen. The stent bridges the lesion and serves to hold tissue in place and possesses sufficient strength to support the wall of the vessel, thereby holding the vessel open so that blood may flow freely. Several types of stents designed for delivery and expansion via a balloon catheter are known in the art.

In use, a stent is typically loaded and crimped onto the balloon portion of the catheter and advanced to a location inside the artery after a PTCA or PTA procedure. The stent is then implanted in the artery and expanded to a larger diameter by means of the catheter balloon. However, if the stent is not securely crimped onto the catheter balloon, the stent may move or even slide off the catheter while the catheter is advanced in the patient's vasculature. Such a circumstance creates a situation where the stent may migrate downstream in the artery and may block the flow of blood, thus necessitating emergency procedures to remove the stent.

Crimped stents used in interventional procedures may be either pre-crimped about the catheter by the supplier or alternatively may be crimped on-site by medical personnel. If pre-crimped stents are used, generally a sufficient supply of pre-loaded catheters must be maintained in order to ensure that a properly sized stent-catheter is available when needed. Maintaining such an inventory can sometimes be expensive. The expense associated with maintaining a large inventory may be reduced by stocking separate catheters and stents, and having the physician or an assistant crimp the appropriate stent on the selected catheter prior to the procedure. In the past, crimping of the appropriate stent onto the catheter was done by hand or with the aid of sterile pliers. Problems sometimes associated with hand-crimping the stent to the catheter include the inability to provide a controlled, uniform, degree of force to obtain a secure uniform crimp over the length of the stent. The crimping problem can be exacerbated by the small size of the stents which are typically about 3–4 millimeters in diameter and 1–10 centimeters in length. Other problems encountered are non-uniform crimping, the inability to determine if a reliable crimp has been achieved, and possible damage to the stent or catheter which can render either or both devices inoperable.

Several devices have been developed in an attempt to address these problems. One such device which addresses these problems is described in U.S. Pat. No. 5,437,083 to Williams et al. The Williams device utilizes a series of plates which have substantially flat and parallel surfaces that move in a rectilinear fashion with respect to each other. A stent bearing catheter is placed between these surfaces to affix the stent onto the outside of the catheter by the relative motion between the plates. As the plates move, a uniform compressive force is applied along the length of the stent to achieve a uniform crimp.

Stents with a uniform crimp may still occasionally slide off of the balloon portion of the catheter which can cause unwanted complications. It is believed that this problem may occur due to the fact that a stent uniformly crimped along its length forms a smooth continuous metal interface with the balloon and therefore may not always generate sufficient frictional resistance to remain positioned on the balloon. This problem usually arises only in certain circumstances, such as when the stent encounters obstacles such as hardened plaque or flaps of tissue partially torn from a vessel wall. Thus, there remains room for improvement in the art. Where stents are supplied pre-crimped to a catheter balloon as part of a stent delivery system, there is a need for a crimping device which will create high frictional resistance between the stent and the balloon and thereby improve stent security on the balloon. In situations where the expense of maintaining an inventory of stent delivery systems is a concern, what is needed in order to rectify both the inventory control problem and the occasional stent slippage problem is a simple, preferably hand-held and single use disposable device that crimps the stent in such a manner as to provide high frictional resistance between the stent and the catheter balloon.

SUMMARY OF THE INVENTION

The present invention provides a stent crimping device that may be used by the physician or other medical personnel to securely crimp a stent onto a balloon catheter prior to an interventional procedure. One object of the present invention is to provide circular stepped crimps at each end of the stent and along predetermined locations along the length of the stent. The number of intermediate circular stepped crimps can vary depending on the length of the stent. The circular stepped crimps provide points of high frictional resistance which significantly reduce the possibility that the stent will slip off of the catheter balloon when being delivered for an interventional procedure. Another object of the invention is to provide a simple hand-held crimping device that may be used on-site with a variety stents and delivery catheters thus obviating the need to stock a large inventory of pre-crimped stent/catheter devices.

In one embodiment of the present invention, the stent crimping device is made of a pair of sliding plates each having a number of raised, narrow ribs. The plates are oriented so that the narrow ribs face each other in a mutually opposed relationship. A stent bearing catheter may be placed between the opposing ribs such that the longitudinal axis of the stent is perpendicular to that of the ribs. Upon receipt of the stent bearing catheter, the sliding plates are pressed together and moved relative to one another thereby allowing the ribs to create the stepped circular crimps on the stent.

In a second embodiment, the stent crimping device includes an upper member having a number of downward facing concave semicircular crimping sectors and a lower member having a number of upward facing concave semicircular crimping sectors. The upper and lower members are oriented in a housing such that the upward and downward facing crimping sectors are mutually opposed to each other. In use, a stent bearing catheter is placed between the upper and lower members and the members are pressed together with a controlled degree of force to cause the crimping sectors to engage and form the semicircular stepped crimps on the stent.

While the embodiments described here are intended for use as hand-held devices, as will be apparent to those skilled in the art, the concept of a stepped circular crimp, whether it be rolled into a stent with straight ribs or impressed with semicircular sectors, may be readily adapted to high volume production machinery as well.

These and other advantages of the present invention will become more apparent from the following detailed description thereof when taken in conjunction with the following drawings.

BRIEF DESCRIPTION OF THE DRAWINGS

FIG. 1 is a perspective view of one embodiment of a stent crimping device made in accordance with the present invention.

FIG. 2 is a perspective view of the horizontally sliding plate, the spring loaded vertically sliding plate, and housing of FIG. 1.

DETAILED DESCRIPTION OF THE PREFERRED EMBODIMENTS

Figure 5:
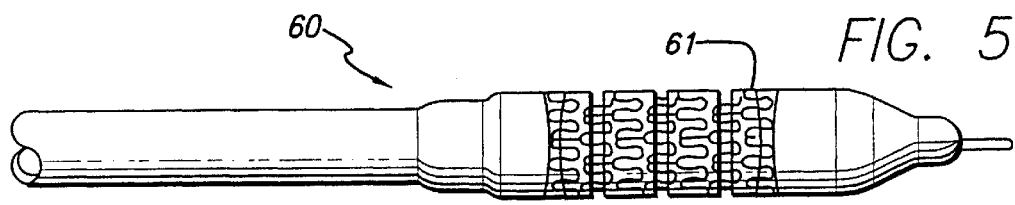
FIG. 5 is a side view of a stent bearing catheter showing a stent with circular stepped crimps formed by the present invention.

As shown in FIGS. 1 and 2, one embodiment of a stent crimping device 10 includes generally, a housing 30, a horizontally sliding plate 20, a vertically sliding plate 40, and a push plate 50. Horizontally sliding plate 20 includes a first substantially flat surface 22 and a plurality of narrow ribs 24. Horizontally sliding plate 20 further includes a pair of slide rails 26. Similar to horizontally sliding plate 20, vertically sliding plate 40 includes a second substantially flat surface 42 and a plurality of narrow ribs 44. The narrow ribs 24 and 44 each have a longitudinal axis of symmetry and are arranged on the horizontally and vertically sliding plates in a substantially parallel configuration with predetermined spacing between the axes. The ribs are placed on the sliding plates such that a circular crimp will be formed at each end of a stent 61 (FIG. 5). Circular crimps at the distal and proximal ends of a stent aid when introducing the stent bearing catheter 60 (FIG. 5) into a guiding catheter and/or into the patient's vasculature. The number of ribs located between the ends of the stent varies depending on the length of the stent. The ribs may be formed integrally with the respective horizontally and vertically sliding plates or may be formed as discrete components which are attached to the horizontally and vertically sliding plates by conventional means such as adhesives, ultrasonic welding, or fasteners.

Figure 6:
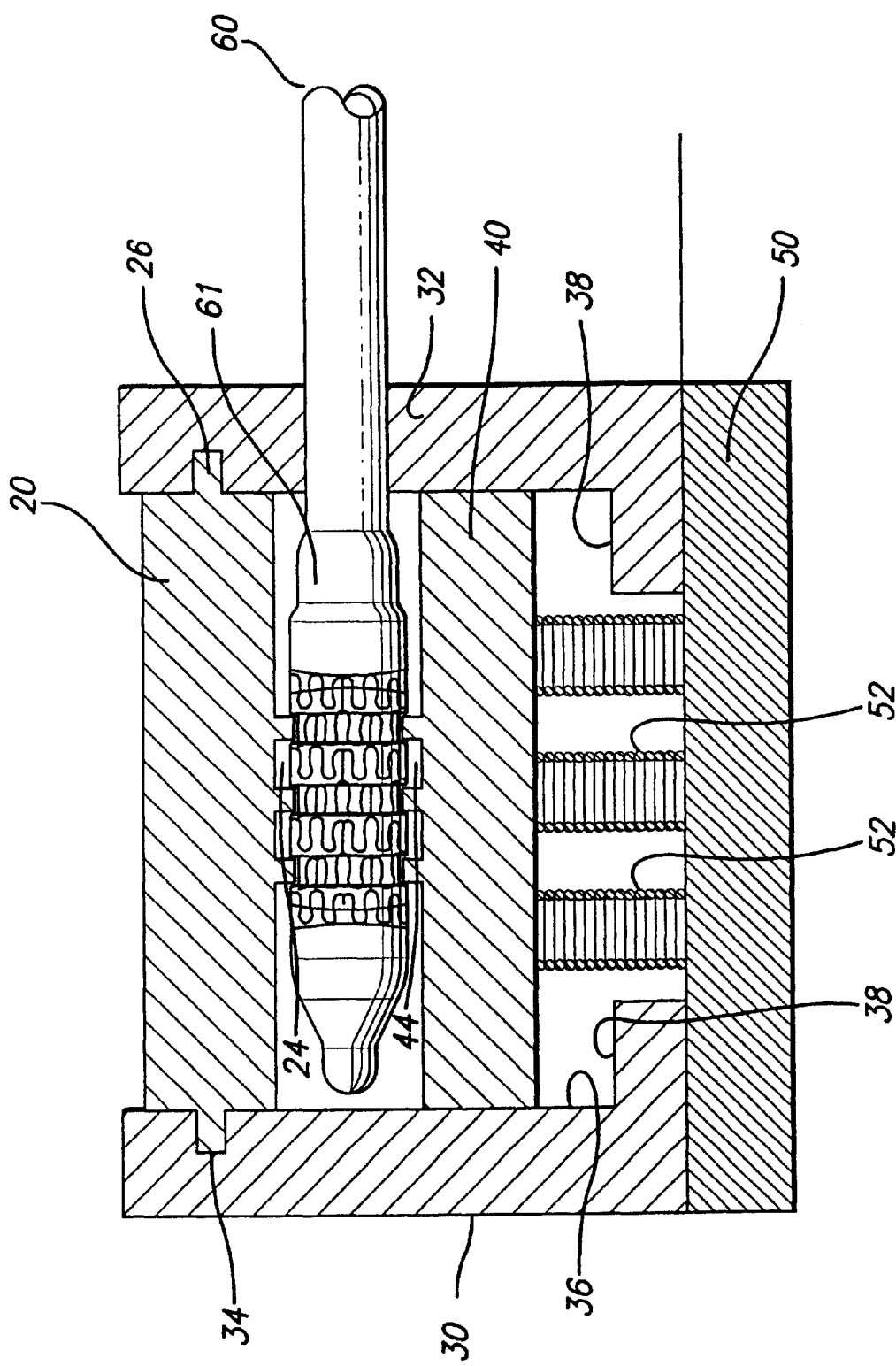
FIG. 6 is a partial cross-sectional view showing a stent bearing catheter being crimped within a stent crimping device similar to the one shown in FIGS. 1 and 2.

The housing 30 serves to hold the horizontally sliding plate 20 and vertically sliding plate 40 such that the first flat surface 22 opposes the second flat surface 42. In this arrangement, the ribs 24 and 44 of the horizontally and vertically sliding plates oppose each other in an axial spaced relationship. The housing 30 also allows horizontally sliding plate 20 to move horizontally relative to the vertically sliding plate 40 and further allows vertically sliding plate 40 to move vertically relative to the horizontally sliding plate 20. As shown in FIG. 2, the housing is U-shaped and includes grooves 34 for receiving the slide rails 26 of horizontally sliding plate 20. The housing also includes planar walls 36 for slidable receipt of the vertically sliding plate 40. A pair of flanges 38 retain the vertically sliding plate 40 within the housing 30. Planar walls 36 are of sufficient depth to allow a stent bearing catheter 60 to be placed between mutually opposing ribs 24 and 44 of the respective horizontally and vertically sliding plates. The housing 30 further includes a slotted opening 32 through which the stent bearing catheter may pass. The stent crimping device 10 also includes a spring loaded push plate 50 attached to the vertically sliding plate 40. A number of springs 52 are attached to the push plate 50 and vertically sliding plate 40 as is shown in FIG. 6. The push plate 50 helps to produce a uniform crimp by providing a degree of feedback or "feel" in response to the force applied to the stent during crimping.

The device is operated as follows. A stent bearing catheter 60 is inserted through the opening 32, and rests between plates 20 and 40. The operator holds the catheter so that the longitudinal axis of the catheter is approximately perpendicular to the longitudinal axes of ribs 24 and 44. The operator then applies force to push plate 50 which forces the vertically sliding plate 40 upwards along the planar walls 36 so that the stent is engaged by mutually opposing ribs 24 and 44. Further application of force causes the opposing ribs 24 and 44 to selectively crimp portions of the stent on to the catheter balloon. When the springs 52 of the push plate 50 are fully depressed, the operator will "feel" the springs reach their solid height and will thereby know that sufficient force has been applied to the stent. Horizontally sliding plate 20 is then moved horizontally or laterally relative to vertically sliding plate 40. Horizontally sliding plate 20 slides along grooves 34 in the U-shaped housing 30 via slide rails 26. As the plate 20 moves laterally relative to plate 40, the stent is rolled along ribs 24 and 44, thereby creating a uniform circular stepped crimp.

For ease of use, the embodiment of FIGS. 1 and 2 is sized to fit into a user's palm, thereby allowing for convenient one-handed operation. While the housing 30 rests in the user's palm, the horizontally sliding plate 20 may be reciprocated by the user's thumb while the user's fingers may apply pressure to push plate 50 attached via springs 52 to vertically sliding plate 40. When the device is used in this manner, one hand remains free to guide the stent bearing catheter through the opening 32 in the housing 30, between the plates 20 and 40, while holding the catheter approximately parallel to the opposing ribs 24 and 44 during the crimping operation.

Figure 3:
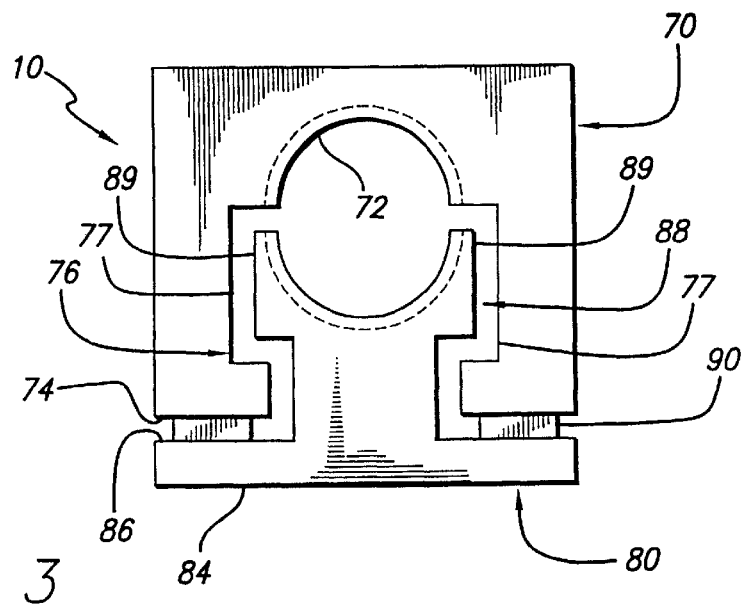
FIG. 3 is a front view of a second embodiment of a stent crimping device made in accordance with the present invention.
Figure 4:
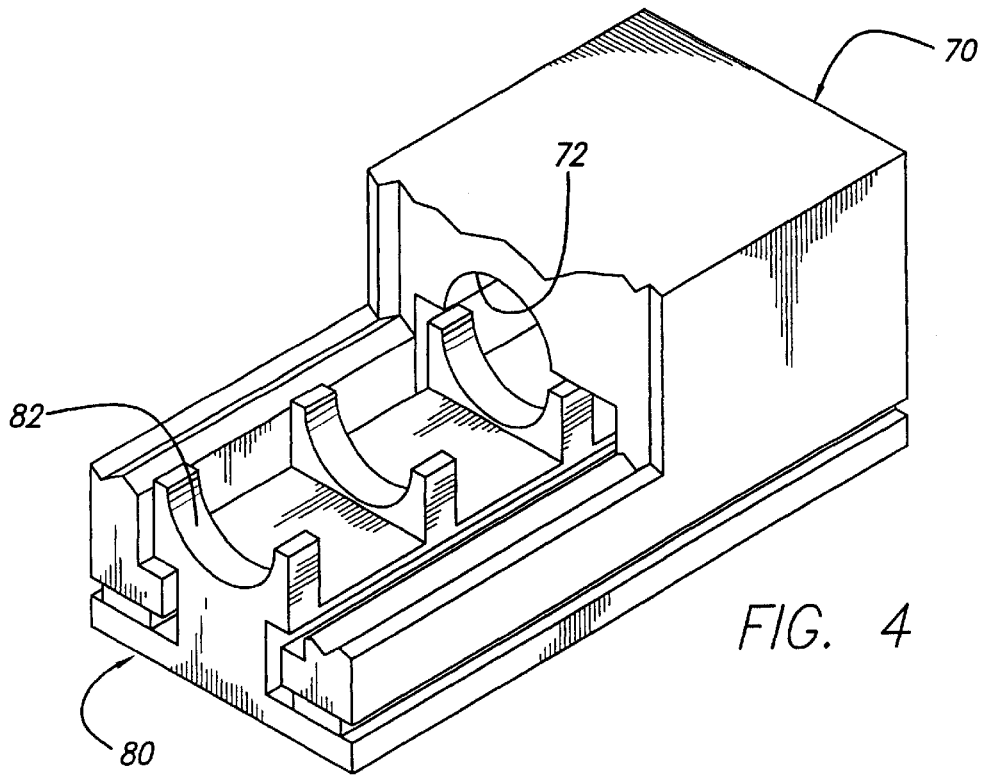
FIG. 4 is a partial cutaway perspective view of the stent crimping device shown in FIG. 3.

Turning now to FIGS. 3 and 4, another embodiment of a stent crimping device made in accordance with the present invention includes an upper member 70, a lower member 80, and a compressive member 90. Lower member 80 includes a push plate 84, a bearing surface 86 to which is affixed compression member 90, a rectangular protrusion 88 which includes walls 89, and a plurality of upward facing semicircular concave crimping sectors 82. Upper member 70 includes a rectangular bore 76 which includes walls 77 for engagement with rectangular protrusion 88, a bearing face 74 which bears against the compression member 90, and a plurality of downward facing semicircular concave crimping sectors 72.

Crimping sectors 72 and 82 have a preferred arc length of about 180 degrees. However, this is not required since arc lengths as short as 45 degrees may be used. Crimping sectors 72 and 82 are configured such that they are substantially parallel in a predetermined spaced relationship. Further, crimping sectors 72 and 82 are arranged in a mutually opposed relationship, i.e. each crimping sector in lower member 80 is paired with a counterpart crimping sector in upper member 70. Similar to the embodiment described previously, the crimping sectors are arranged at each end of the stent with the number of sectors located between the ends of the stent dependant on the length of the stent. In the embodiment shown in FIGS. 3 and 4, the crimping sectors 72 and 82 are integrally formed with respective upper and lower members 70 and 80. However, as will be appreciated by those skilled in art, the crimping sectors may also be produced as separate components which are attached to their upper and lower members 70 and 80 respectively.

A compression member 90 provides an interface between the upper and lower members. Compression member 90 allows an operator to provide a controlled degree of force during the crimping operation. In one preferred embodiment, compression member 90 is a snap-action spring. However, compression member 90 need not be a snap-action spring but rather may comprise any suitable compressive device including compressible elastomeric materials or coil springs.

To use the crimping device 10 shown in FIGS. 3 and 4, an operator holds the device 10 in the palm of one hand with fingers curled around the device to make contact with push plate 84. With a free hand the operator inserts a stent bearing catheter within the semicircular opening formed by the crimping sectors. The operator then applies pressure to push plate 84 causing lower member walls 88 to slide vertically upwards along upper member walls 77. The relative vertical movement of the upper and lower members causes the opposed crimping sectors 72 and 82 to engage the stent. Upon application of sufficient force, the sectors form a semicircular depression or step in the stent, thereby securely fixing the stent to the catheter balloon. When sufficient force has been applied to securely crimp the stent in position, the snap-action spring 90 will snap to a quasi-stable position. Upon hearing and/or feeling the positive snap, the operator will then relax his fingers allowing spring 90 to snap back to its initial position. The catheter is then removed from the crimping device. This embodiment of the crimping device will produce a stepped circular crimp in the stent with a nonuniform pressure distribution between the stent and catheter balloon, as shown in FIG. 5. By contrast, the crimping device shown in FIGS. 1 and 2 produces a stepped-circular crimp with a uniform pressure distribution.

The crimping devices of the present invention can be manufactured by injection molding an elastomeric or plastic material to form the various components. After molding, the stent crimping devices are packaged in a sealed clear plastic bag (polyethelene), and are then sterilized by irradiation techniques well known to those skilled in the art.

While the stent described for use with the crimping device of the present invention is intended to serve as an intraluminal graft within a blood vessel, and the balloon delivery catheter is of the type commonly used in coronary angioplasty, it will be appreciated by those skilled in the art that modifications may be made to the present invention to allow the present invention to be used to crimp any type of graft or prosthesis. The present invention is not limited to crimping stents that are deployed in a patient's vasculature, but has wide application to grafts or prostheses delivered into various body lumens. Other modifications can be made to the present invention by those skilled in art without departing from the scope thereof.

What is claimed:

1. An apparatus for crimping a stent on to a catheter, comprising:
   an upper member including a plurality of downward facing semicircular crimping sectors wherein the sectors are parallel and of predetermined spacing;
   a lower member including a plurality of upward facing semicircular crimping sectors wherein the sectors are parallel and of predetermined spacing;
   means for configuring the upper and lower members such that the downward and the upward facing crimping sectors are mutually opposed in an axial spaced relationship such that a catheter having a stent disposed about its periphery may be received between the mutually opposed crimping sectors,; and
   a compression member for maintaining the mutually opposed crimping sectors in a mutually opposite arraignment for receiving the stent and catheter, the compression member being compressible by an externally applied force to move the crimping sectors towards one another to provide a controlled crimping force to crimp the stent onto the outside of the catheter, wherein the compression member has a thickness to maintains, the upper and lower members in a mutually opposite arraignment for receiving the stent and catheter and is compressible to a certain thickness to prevent additional external crimping force to be applied to the stent and catheter.

2. The crimping apparatus of claim 1, wherein the semicircular sectors have an arc length of 180 degrees.

3. The crimping apparatus of claim 1, wherein the crimping sectors are substantially convex in shape.

4. The crimping apparatus of claim 1, wherein the crimping sectors are formed integrally with the upper and lower members.

5. The crimping apparatus of claim 1, wherein the upper and lower members are sized to fit in a human hand.

6. The crimping apparatus of claim 1, wherein the compression member comprises a plurality of springs attached to the upper member; and a push plate attached to the springs.

7. The crimping apparatus of claim 4, wherein the upper and lower members are made of elastomeric material.

8. The crimping apparatus of claim 1, wherein the compression member is disposed between the lower member and the upper member.

9. The crimping apparatus of claim 1, wherein the compression member comprises a plurality of springs disposed between the lower member and the upper member.

10. An apparatus for crimping a stent on to a catheter, comprising:

an upper member including a plurality of crimping sectors;

a lower member including a plurality of crimping sectors, the upper and lower members being positioned such that crimping sectors of each upper and lower members are maintained a mutually opposed and spaced relationship such that a catheter having a stent disposed about its periphery may be received between the mutually opposed crimping sectors; and a compression member disposed between the upper member and lower member for maintaining the mutually opposed crimping sectors in the mutually opposite arraignment for receiving the stent and catheter and being compressible by an externally applied force to move the crimping sectors towards one another to provide a controlled crimping force to crimp the stent onto the catheter, wherein the compression member has a first position in which the compression member maintains the crimping sectors of the upper and lower members in a mutually opposite arraignment for receiving the stent and catheter and a second position in which the compression member is fully compressed to prevent additional external crimping force to be applied to the stent and catheter.

11. The crimping apparatus of claim 10, wherein the compression member is made from an elastomeric material.

12. The crimping apparatus of claim 10, wherein the compression menber comprises a plurality of springs.

13. The crimping apparatus of claim 10, wherein the crimping sectors of the upper and lower members are substantially parallel and of predetermined spacing.

14. The crimping apparatus of claim 10, wherein the semicircular crimping sectors have an arc length of 180 degrees.

15. The crimping apparatus of claim 10, wherein the crimping sectors are substantially convex in shape.

* * * * *

UNITED STATES PATENT AND TRADEMARK OFFICE
CERTIFICATE OF CORRECTION

PATENT NO.     : 6,481,262 B2
DATED          : November 19, 2002
INVENTOR(S)    : Denise Ching et al.

It is certified that error appears in the above-identified patent and that said Letters Patent is hereby corrected as shown below:

Column 6,
Line 51, change "maintains" to read -- maintain --.

Signed and Sealed this

Twenty-fifth Day of March, 2003

JAMES E. ROGAN
*Director of the United States Patent and Trademark Office*